United States Patent [19]
Anderson

[11] Patent Number: 5,925,078
[45] Date of Patent: Jul. 20, 1999

[54] METHODS AND APPARATUS FOR JOINING COLLAGEN-CONTAINING MATERIALS

[75] Inventor: R. Rox Anderson, Lexington, Mass.

[73] Assignee: The General Hospital Corporation, Boston, Mass.

[21] Appl. No.: 08/744,518

[22] Filed: Nov. 4, 1996

Related U.S. Application Data

[63] Continuation of application No. 08/184,008, Jan. 19, 1994., Pat. No. 5,571,216

[51] Int. Cl.$^6$ ........................................................ A61F 2/54
[52] U.S. Cl. ................................. 623/66; 606/8; 606/213
[58] Field of Search ........................... 623/11, 66; 606/8, 606/213; 424/422–424

[56] References Cited

U.S. PATENT DOCUMENTS

| | | | |
|---|---|---|---|
| 4,597,762 | 7/1986 | Walter et al. | 623/1 |
| 4,633,870 | 1/1987 | Sauer | 128/303.1 |
| 4,672,969 | 6/1987 | Dew | 128/397 |
| 4,799,479 | 1/1989 | Spears | 128/303.1 |
| 4,854,320 | 8/1989 | Dew et al. | 606/213 |
| 4,892,098 | 1/1990 | Sauer | 606/18 |
| 4,911,710 | 3/1990 | Milthorpe et al. | 623/66 |
| 4,929,246 | 5/1990 | Sinofsky | 606/8 |
| 5,002,583 | 3/1991 | Pitaru et al. | 623/66 |
| 5,108,424 | 4/1992 | Hoffman et al. | 623/1 |
| 5,141,747 | 8/1992 | Scholz | 424/424 |
| 5,334,191 | 8/1994 | Poppas et al. | 606/12 |
| 5,354,336 | 10/1994 | Kelman et al. | 623/6 |

FOREIGN PATENT DOCUMENTS 0 330 344 A2  8/1989  European Pat. Off. .

OTHER PUBLICATIONS

Spikes et al., "Effects of Photodynamic Treatment on the Thermal–Mechanical Properties of Collagen", *Abstracts of the 21st Annual Meeting of the American Society for Photobiology,* TPM–F36 (Jun. 26–30, 1993).

DeCoste et al., "Dye–Enhanced Laser Welding for Skin Closure," *Lasers in Surgery and Medicine,* 12:25–32, (1992).

Lemole, Jr. et al., "Preliminary evaluation of collagen as a component in the thermally–induced 'weld'," *Lasers in Dermatology and Tissue Welding, SPIE 1422*:116–122 (1991).

Oz et al., "Tissue soldering by use of indocyanine green dye–enhanced fibrinogen . . . ," *J. Vasc. Surg.,* 11:718–725 (May 1990).

Goldstein et al., "Development of a Reconstituted Collagen Tendon Prosthesis," *The Journal of Bone and Joint Surgery,* 71–A:1183–1191 (Sep. 1989).

Mininberg et al., "Laser Welding of Pedicled Flap Skin Tubes," *The Journal of Urology,* 142:623–625 (Aug., 1989).

Grubbs, Jr. et al., "Determinants of Weld Strength in Laser–Assisted Microvascular Anastomosis," *Current Surgery,* 46:3–5 (Jan./Feb. 1989).

(List continued on next page.)

*Primary Examiner*—Michael J. Milano
*Attorney, Agent, or Firm*—Fish & Richardson P.C.

[57] ABSTRACT

A method of permanently joining a first collagen-containing material to a second collagen-containing material, each material having free ends of collagen fibrils at a surface, by bringing the free ends of collagen fibrils at the surfaces of the first and second materials into contact, heating the first and second materials for a time and to a temperature sufficient to permanently join the first and second materials at an area of contact of the free ends, wherein the temperature is above a melting temperature of the collagen fibril free ends, and below a melting temperature of intact collagen fibrils, such that collagen fibrils in the first and second materials are not denatured except at their free ends, and optionally thereafter crosslinking the collagen along the area of contact.

7 Claims, 4 Drawing Sheets

OTHER PUBLICATIONS

Murray, et al., "Crosslinking of Extracellular Matrix Proteins: A Preliminary Report on a Possible . . . ," *Lasers in Surgery and Medicine,* 9:490–496 (1989).

Chuck et al., "Dye–Enhanced Laser Tissue Welding," *Lasers in Surgery and Medicine,* 9:471–477 (1989).

Oz et al., "In Vitro Comparison of Thulium–Holmium–Chromium: YAG and Argon Ion Lasers for Welding of Biliary Tissue," *Lasers in Surgery and Medicine,* 9:248–253 (1989).

Gilbert et al., "Laser–Assisted Vasovasostomy," *Lasers in Surgery and Medicine,* 9:42–44 (1989).

Fujitani et al., "Biophysical Mechanisms of Argon Laser–Assisted Vascular Anastomoses," *Current Surgery,* pp. 119–123 (Mar./Apr. 1988).

Poppas et al., "Laser Welding in Urethral Surgery: Improved Results with a Protein Solder," *The Journal of Urology,* 139:415–417, (Feb. 1988).

Kopchok et al., "$CO_2$ and Argon Laser Vascular Welding: Acute Histologic and Thermodynamic Comparison," *Lasers in Surgery and Medicine,* 8:584–588 (1988).

White et al., "Mechanism of Tissue Fusion in Argon Laser–Welded Vein–Artery Anastomoses," *Lasers in Surgery and Medicine,* 8:83–89 (1988).

Anand et al., "Laser Balloon Angioplasty: Effect of Constant Temperature Versus Constant Power . . . ," *Lasers in Surgery and Medicine,* 8:40–44 (1988).

Grubbs, Jr. et al., "Enhancement of $CO_2$ Laser Microvascular Anastomoses by Fibrin Glue[1]," *Journal of Surgical Research,* 45:112–119 (1988).

Kopchok et al., "Thermal Studies of In–Vivo Vascular Tissue Fusion by Argon Laser," *Journal of Investigative Surgery,* 1:5–12 (1988).

White et al., "Argon laser–welded arteriovenous anastomoses," *Journal of Vascular Surgery,* 6:447–453 (Nov. 1987).

White et al., "Comparison of Laser–Welded and Sutured Arteriotomies," *Arch. Surg.,* 121:1133–1135 (Oct. 1986).

Schober et al., "Laser–Induced Alteration of Collagen Substructure Allows Microsurgical Tissue Welding," *Science,* 232:1421–1422 (Jun. 13, 1986).

Abergel et al., "Skin closure by Nd: YAG laser welding," *Journal of the American Academy of Dermatology,* 14:810–814 (May 1986).

Vale et al., "Microsurgical Anastomosis of Rat Carotid Arteries with the $CO_2$ Laser," *Plastic and Reconstructive Surgery,* 77:759–766 (May 1986).

Kopchok et al., "Argon laser vascular welding: The thermal component," *Lasers in Medicine, SPIE* 712:260–263 (1986).

Nimni, "The Molecular Organization of Collagen and its Role in Determining . . . ," *Biorheology,* 17:51–82 (1980).

Jain et al., "Repair of small blood vessels with the Neodymium–YAG laser: A preliminary report," *Surgery,* 85:684–688 (Jun. 1979).

Tanzer, "Cross–Linking of Collagen," *Science,* 180:561–566 (May 1973).

Oz et al. "Tissue Soldering By Use of Indocyanine Green Dye–Enhanced Fibrinogen with the Near Infrared Diode Laser," *Journal of Vascular Surgery,* 11–5:718–725 (May 1990).

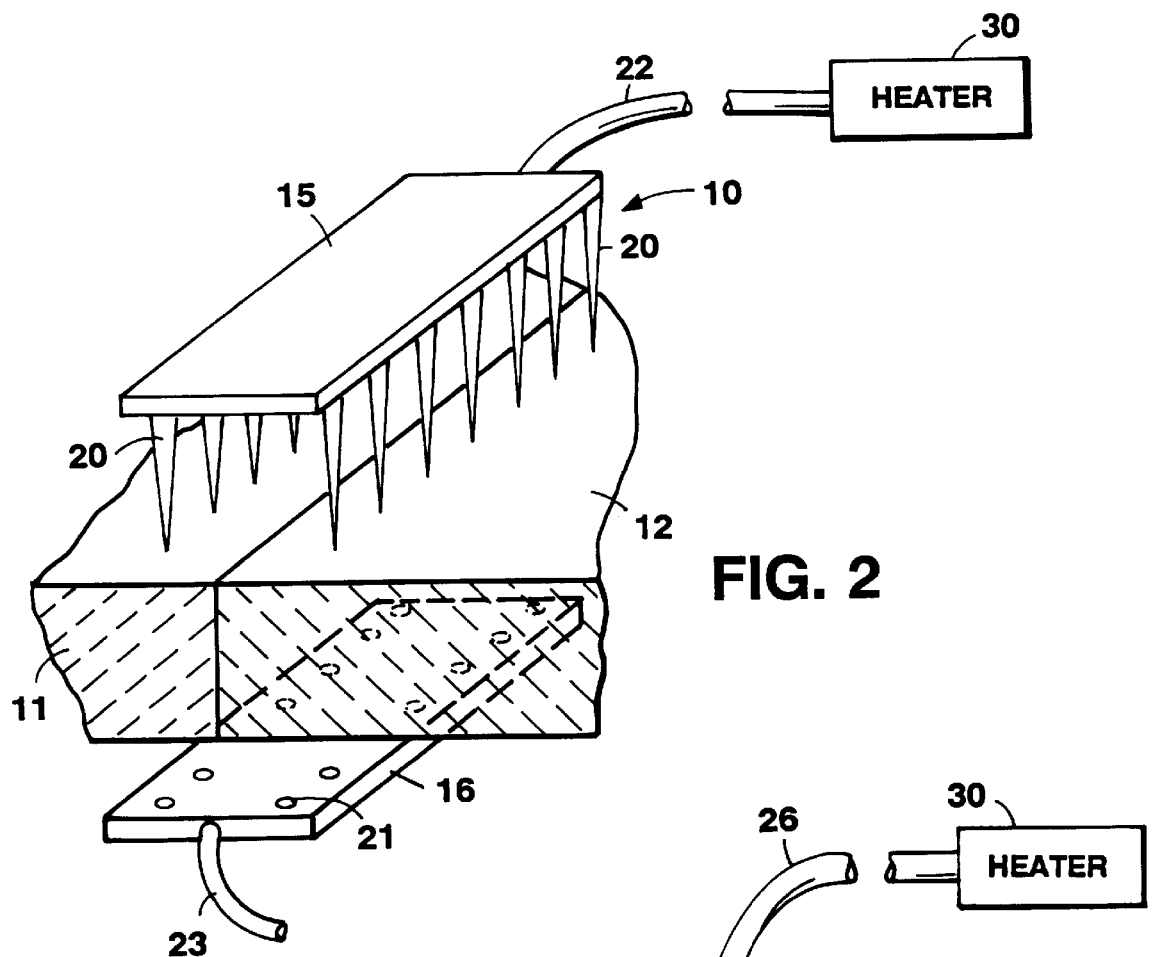
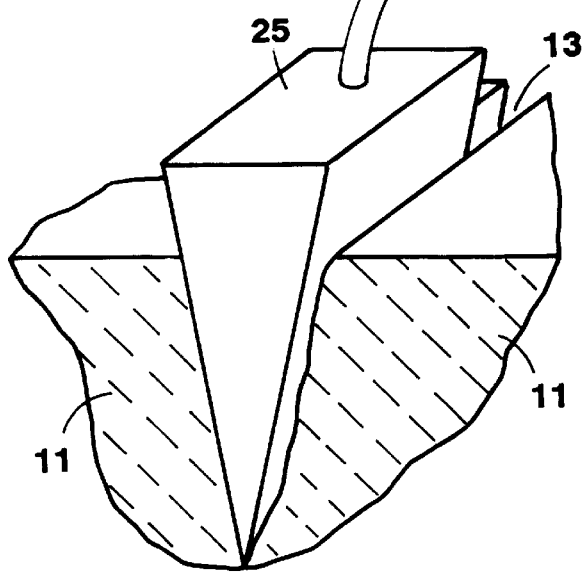

METHODS AND APPARATUS FOR JOINING COLLAGEN-CONTAINING MATERIALS

This is a continuation of application Ser. No. 08/184,008 filed Jan. 19, 1994 now U.S. Pat. No. 5,571,216.

This invention was made with Government support under Contract N00014-86-K-00117 awarded by the Department of the Navy. The Government has certain rights in the invention.

BACKGROUND OF THE INVENTION

This invention relates to methods for permanently joining collagen-containing materials.

Many medical procedures necessitate joining two separate tissue pieces in order to promote wound healing or fusion of the pieces. In addition, many procedures require the connection of a prosthesis to a tissue within the body. These procedures can be done with conventional suturing, stapling, or with newer methods of suture-less tissue repair. However, conventional suturing techniques are time-consuming, and sutures and staples introduce foreign materials into the tissue, thus increasing the risk of infection or adverse immunological reaction. Suturing also disrupts the normal growth and cellular organization of the tissue and increases the risk of scar tissue formation which can interfere with the function of the native tissue, e.g., by partially occluding flow of blood through a sutured vessel. Additionally, scar tissue may create undesired irregularities in the skin. Sutures also leak, which can cause complications, e.g., gastric fluid leakage after gut surgery.

Suture-less joining of tissues has been achieved by "gluing" tissue segments together, using either foreign substances such as cyanomethacrylates, or naturally occurring compounds such as thrombin and fibrin. In addition, suture-less joining or "welding" of tissues has been accomplished with lasers, such as $CO_2$, Nd:YAG, THC:YAG, argon, and near infra-red diode lasers. For example, welding of connective tissues was described by Jain, *J. Microsurg.* 1:436–439 (1980) and Dew et al., *Lasers Surg. Med.* 3:135 (1983), who used low-power lasers, e.g., argon-ion, Nd:YAG, and $CO_2$ lasers, to permanently attach well-approximated tissues.

Only connective tissues can be welded, including blood vessel walls, tendon, fascia, some muscle, skin, biliary tissue, epineurium, nerves, urethra, fallopian tube, vas deferens, and gut. Fat and highly cellular tissues do not weld. As a result, it has been suggested that some type of collagen is involved. For example, Schoeber at al., *Science*, 232:1421–1422 (1986) showed by electron microscopy that denatured collagen was present in the region of argonion laser welded tissue. However, Schoeber's study showed gross thermal denaturation extending hundreds of $\mu m$ on either side of the weld anastomosis. Further, it is known that laser welding results in the formation of collagen-collagen and collagen-elastin bonds (White et al., *Lasers Sura. Med.*, 8:83–89 (1988)).

One use for tissue welding that has been of interest is vascular repair. White et al. (1988), showed that argonion laser welded vessels heal with the same strength over time as sutured vessels (after the sutures were removed), but with less foreign body reaction and better mechanical compliance. White et al., *J. Vasc. Surg.* 6:447–453 (1987), also welded arteriovenous shunts in patients requiring hemodialysis.

In spite of improvements in technique, laser tissue welding is not widely used because it is technically demanding, and the welds are weak. For example, White et al., *Lasers Surg. Med.*, 6:137–141 (1986), reported that the tensile strength of laser-welded arteries was less than that of sutured arteries during the initial weeks following the surgical procedure. Thus, researchers have attempted to strengthen laser welds by applying fibrinogen (Oz et al., *J. Vasc. Surg.*, 11:718–725 (1990)), fibrin (Grubbs et al., *J. Surg. Res.*, 45:112–119 (1988)), or albumin (Poppas et al., *J. Urology*, 139:415–417 (1988)) to the weld site. In addition, as described, e.g., in Oz et al., (1990), and Decoste et al., *Lasers Surg. Med.*, 12:25–32, (1992), dyes, such as fluorescein isothiocyanate and indocyanine green (IG), have been used to enhance absorption of laser radiation at the site to be welded.

SUMMARY OF THE INVENTION

The present invention allows the permanent joining or "welding" of collagen-containing materials, e.g., Type 1 collagen-containing biological connective tissues or prostheses, in novel ways that produce high weld strength and limit any damage, e.g., tissue denaturation, to an extremely narrow region at the "weld seam" formed between the two materials. To achieve this result, the invention exploits fundamental characteristics of collagen.

The invention provides methods for surgical repair of connective tissues that are faster, result in less or no scarring, and provide overall medical cost-savings compared to known methods. In addition, certain tissue repair, e.g., tendon repair, is very difficult using sutures, and results in slow healing. The invention provides substantially improved methods to achieve permanent repairs of these, and other tissues. The scant 1 to 2 $\mu m$ zone of denaturation necessary for welding heals with minimal inflammation or foreign body reaction. In skin, the methods of the invention also provide better cosmetic results than prior methods of surgical repair.

In general, the invention features a method of permanently joining a first collagen-containing material to a second collagen-containing material, each material having free ends of collagen fibrils at a surface, by bringing the free ends of collagen fibrils at the surfaces of the first and second materials into contact, heating the first and second materials for a time and to a temperature sufficient to permanently join the first and second materials at an area of contact of the free ends, wherein the temperature is above a melting temperature of the collagen fibril free ends, and below a melting temperature of intact collagen fibrils, such that collagen fibrils in the first and second materials are not denatured except at their free ends.

As discussed further below, the melting temperatures of collagen fibril free ends and intact collagen fibrils vary depending upon the particular material and duration of heating time. In practice, the melting temperature of collagen fibril free ends is substantially below, e.g., about 10° C. or more, that of intact collagen fibrils.

In a further embodiment, the invention features the additional step of crosslinking the collagen along the area of contact between the two materials after the heating step is complete. Crosslinking can be achieved by applying a crosslinking agent, e.g., glutaraldehyde, formaldehyde, dihydroxyacetone, or a keto-sugar, to the area of contact. crosslinking can also be achieved by applying ultraviolet radiation to the area of contact, or by applying a photodynamic photosensitizer and then applying radiation to the area of contact. The photodynamic photosensitizer can be a phthalocyanine, chlorin, porphyrin, 8-methoxypsoralen, xanthene dye, or thiazine dye, e.g, methylene blue.

In these methods, the first and second materials may be the same or different, and preferably contain Type 1 collagen. The first and second materials can both be biological tissues, or the first material may be a biological tissue and the second material may be a collagen-containing prosthesis.

In preferred embodiments, the first and second tissues are heated to a temperature of about 61° C., which varies by a few degrees up or down according to the duration of heating and the type of material joined as described below.

In further aspects of the invention, heating is achieved by electrical resistance, circulating fluid, radio frequency current, microwaves, ultrasound, or infrared or optical radiation. In addition, heating may be achieved with a laser beam, e.g., having a wavelength from 720 nm to 820 nm. When a laser is used, the method can include a further step of applying a dye, e.g., indocyanine green, to the surfaces of the first and second materials prior to heating, wherein the dye has an absorption spectrum maximum corresponding to a wavelength of the laser beam.

The invention also features a further step of quenching, i.e., rapidly cooling, the area of contact between the two materials after they are joined.

Unless defined otherwise, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patents, and patent applications mentioned herein are incorporated by reference. In addition, the materials, methods, and examples are illustrative only and not intended to be limiting.

Other features and advantages of the invention will be apparent from the following detailed description, and from the claims.

DETAILED DESCRIPTION

The drawings are first briefly described.

Drawings

FIG. 2 is a schematic of a needle heating device for use in the methods of the invention.

FIG. 3 is a schematic of wedge-shaped heating device for use in the methods of the invention.

WELDING OF COLLAGEN-CONTAINING MATERIALS

One aspect of the present invention is based on the knowledge that the free ends of Type 1 collagen fibrils denature, or "melt," at a lower temperature than intact collagen fibrils. Such free ends are created by any transection of the fibrils, e.g., by cutting or shearing the fibrils at the surface of a material to be welded. Such free ends may arise accidentally or can be made intentionally, e.g., by an incision. According to the invention, welding is achieved by bringing the free ends at the surfaces of two materials into contact, e.g., by clamping, and preferentially melting these free ends of the collagen fibrils at a temperature below the melting temperature of intact collagen fibrils (tissue shrinkage temperature). The resulting weld consists of gelation between fibrils across the gap resulting mostly from non-covalent bonds.

Temperature

By precisely controlling the temperature to which the collagen-containing materials are heated, i.e., to a temperature at which the free ends of collagen fibrils melt, but substantially below the temperature at which the intact collagen fibrils melt, the surfaces can be preferentially denatured, and thus welded, along their area of contact, i.e., a "weld seam." Any damage to the fibrillar collagen and elastin matrix of the materials is limited to a superficial 1 to 2 $\mu$m layer directly adjacent this seam, i.e., the region of the free ends. This layer is so thin, that the resulting weld seam cannot even be seen under a light microscope. In practice, this temperature falls within a narrow range of about 60° C. to 62° C. This range is based on the recognition that the precise temperature required to limit the desired melting to only the 1 to 2 $\mu$m layer of the free ends varies slightly depending on the length of time the collagen-containing materials are heated, and the nature of the material, as discussed below.

By precisely heating the tissue to the required temperature, the tensile strength of the resulting weld is about 4 to 5 times stronger than prior welding techniques. The method reliably produces welds of greater than 1 kg/cm$^2$ tensile strength, whereas welds attempted at, e.g., over 70° C., have a tensile strength of less than 0.2 kg/cm$^2$.

In addition, different tissues have been found to have slightly different melting temperatures depending on their Type 1 collagen content, and the melting temperature also varies slightly with the age of the material. For example, tendons and skin have a very high collagen content, e.g., 40 to 80%, and have a desired welding temperature at the upper end of the range, e.g., about 62° C. These factors are used to determine the required welding temperature of a particular tissue in a particular patient.

Figure 1:
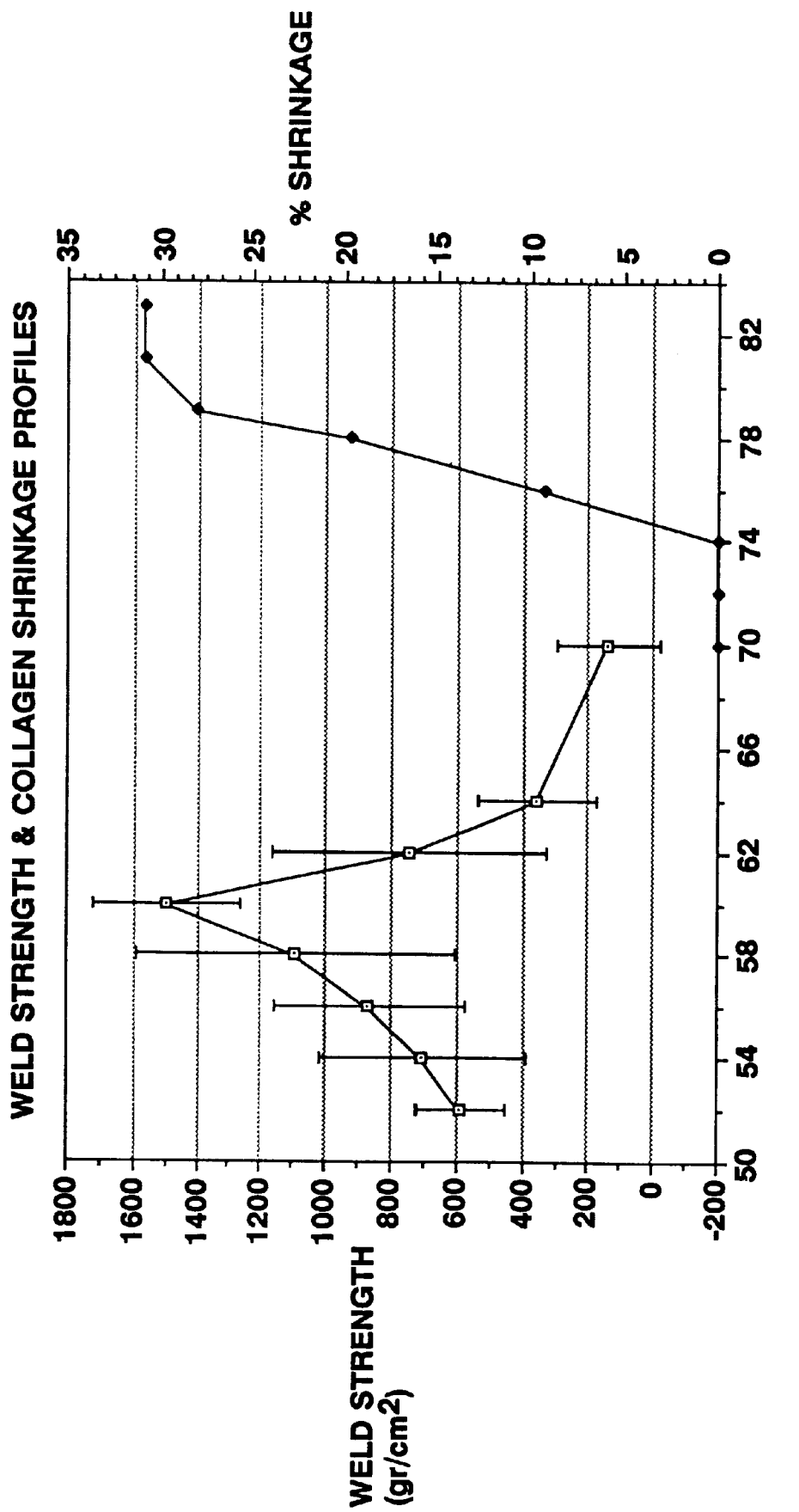
FIG. 1 is a graph showing tensile strength of bovine tendon disc welds as a function of temperature.

The graph of FIG. 1 shows the tensile strength of bovine tendon disc welds as a function of temperature (30 minute heating time; left scale). A narrow temperature region near 60° C. provides the strongest weld for this heating time and tissue. The graph (right scale) also shows that undesirable thermal shrinkage (melting of intact collagen fibrils) begins to occur at about 74° C., which is substantially above the required welding temperature range. The tissue shrinkage temperature also varies with duration of heating.

Timing

In addition to the specific required temperature, the methods of the invention require that the collagen-containing materials be heated uniformly to this precise temperature for a time sufficient to permanently join the surfaces of the two materials. Heating times from a few seconds to tens of minutes are practical, with the actual heating time based on the surgical procedure and type of tissue. For example, for arterial joining, a quick weld, e.g., 30 to 60 seconds, is desired to avoid an overly long stoppage of the blood flow through that artery. For a tendon, a longer welding time, e.g., 1 to 10 minutes, is acceptable.

The required temperature will vary depending on the time selected and the tissue being treated. However, the key parameter is the temperature, which is affected in only a minor way by the welding time. In general, the required temperature will only decrease slightly, e.g., one to two degrees, for a 10-fold increase in the welding time. For example, if the temperature for 30 minutes of heating a particular material is 60° C., it will be about 61° C. or 62° C. for a 3 minute heating time of the same material.

Heating Devices

The uniform and precise heating of the collagen-containing materials can be achieved with any heating device that allows the user to constantly maintain the material at the required temperature. For example, feedback controlled lasers (e.g., diode lasers), microwave, radio frequency, or ultrasound heaters, hyperthermia devices, or contact heaters can be used for the present invention. The heating device is preferably sized and shaped to facilitate treatment of the area to be joined.

The simplest of these heating devices is a contact heater. Such a device generally requires no feedback mechanism to let the operator know the temperature of the tissue. The device is brought to the desired temperature, and is then brought into contact with the two collagen-containing materials. FIG. 2 shows one embodiment of a contact heater within the scope of the present invention. Device 10 is constructed of two parallel rows of numerous hollow needles 20 in a comb-like arrangement in a hollow block 15 that allows free flow of liquid into each of the needles. These needles, which can be stainless steel syringe needles, are arranged in each row in close proximity to each other, e.g., a few millimeters apart, and the two rows are arranged for insertion into tissues 11, 12 on either side of cut surfaces once the tissues are brought into close contact.

In use, the cut surfaces of tissues 11 and 12 are brought into contact, e.g., by clamping or other standard techniques, needles 20 are inserted into and through the two tissues on either side of the apposed cut surfaces, and are supplied through hollow tube 22 and block 15 with a fluid, e.g., water, heated to the desired temperature by a heater 30. The needles thus serve as individual heat sources and bring the tissues to a uniform temperature along the weld seam without overheating. The needles are maintained at the desired temperature, e.g., 60° C., for a set time, e.g., 3 to 5 minutes, and are then removed. The two tissues are then permanently joined along the weld seam. The hot liquid is collected at the other end of the needles by a similar block 16 with holes 21 for receiving each of the needle tips. The collected water is removed through tube 23, e.g., to waste.

The needles can also be made of a solid heat conducting material that conduct the heat from block 15 into the tissue. In such a device, lower block 16 is not required, and the needles do not have to protrude through the tissues 11 and 12. Block 15 can also be heated by other means, e.g., electric resistance heating. In addition, the device can also be arranged in the form of one row of curved needles that enter one tissue and exit the other tissue on the other side of the two apposed surfaces.

Another contact heater within the scope of the invention, which is especially suited for welding an incision in, e.g., skin, is a wedge-shaped probe 25, as shown in FIG. 3. This probe 25 can be hollow, and is made of a heat conducting material, e.g., stainless steel. The probe is maintained at a constant temperature, e.g., by circulating a heated fluid through the probe via a hollow tube 26 that links the probe 25 to heater 30, or by an electrical resistance heating element connected to a current source (not shown).

In use, probe 25 is inserted into incision 13 in tissue 11 and is heated to the desired temperature. The probe is then slowly withdrawn from the incision, allowing the two cut surfaces of the incision to weld together as the wedge is withdrawn. To enhance this welding, the probe may be vibrated at high frequency, e.g., with a piezoelectric device.

The most important aspect of the heating device is the ability to precisely control and maintain the tissue temperature. In more complicated heating devices, e.g., lasers, and radio frequency and microwave heaters, the tissue temperature must be continuously determined to maintain the desired temperature and avoid overheating. For example, far-infrared radiometric feedback can be used to control a laser to perform welding according to the invention. This could be a low-power laser, e.g., a AlGaAs semiconductor diode laser, controlled by a non-contact temperature sensor, capable of maintaining a specific temperature accurately. Anderson et al., *Applied Optics*, 28:2256–2262 (1989) and Vitkin et al., *J. Photochem. Photobiol. B.*, 16:235–239 (1992) describe infrared radiometry for tissue temperature measurement and control during laser heating. Contact temperature sensors, such as thermocouples (e.g., those made by Omega Engineering, Inc., Stamford, Conn.) can also be used to ensure precise control of tissue temperature during the welding process.

Known laser apparatus for welding tubular tissues such as those described in Sauer, U.S. Pat. Nos. 4,633,870, and 4,892,098, can be adapted to provide uniform heating within the preferred temperature range.

One known device that can be modified for use in the present welding methods is a Shaw HOT SCALPEL™ (made by Hemostatix Co., Mountain View, Calif.) which is a feedback controlled diode laser knife that is designed to cut tissues at 90 to 100° C. This device can be modified by standard methods to obtain a device that maintains a tissue temperature, e.g., of 60 to 62° C. Similarly, radio frequency heaters used for hyperthermia treatment can be modified to maintain tissue temperatures in the desired range.

If a laser is used to heat the tissues, it is important to use a laser wavelength that is well absorbed by the material, e.g., tissue, to be welded, or a dye applied to the tissue. It is also important that the light penetrate sufficiently into the tissue. For example, the wavelength range of 720 to 820 nm is a spectral region with good tissue penetration. The absorbance of a particular laser wavelength by a tissue can be enhanced by the use of various dyes that can be applied to the surfaces of the tissue prior to welding. This technique facilitates the selective delivery of laser energy to the surfaces, and thus further reduces the chances of any damage to tissue outside the immediate weld site.

One such dye, a supravital dye, indocyanine green (IG), which has an absorption maximum at 780 to 805 nm in tissue, is particularly suited for laser welding of skin, as described in DeCoste et al., *Lasers Surg. Med.*, 12:25–32 (1992). This dye is preferably used in conjunction with a near-infrared alexandrite laser (e.g., a Schwartz Electro-optics, Inc. model 1-2-3 operated at 780 nm) or a continuous-emitting diode laser operated at a wavelength of about 800 nm. Another dye, fluorescein isothiocyanate (FITC) can be used with an argon laser as described in Chuck et al., *Lasers Surg. Med.*, 9:471–477 (1989).

These dyes, e.g., at a 0.1% solution for IG, can be applied topically to the cut surfaces of the tissues by standard techniques, e.g., filling an incision for a time sufficient for the dye to penetrate the surfaces, e.g., up to 5 minutes and then washing away excess dye with saline, or can be injected with a syringe.

Crosslinking After Welding

Another important feature of the present invention is the discovery that crosslinking the collagen in the weld, e.g., chemically, after heating is completed provides a synergistic effect to produce greatly increased tensile strength, because covalent bonds are added to the weak non-covalent interactions involved in gelation alone. In contrast, crosslinking before the heating step decreases or actually prevents welding, because the Type 1 collagen fibrils are unable to melt after crosslinking.

Crosslinking increases weld tensile strength by an additional factor of about 5 after the thermal welding. Welded and then crosslinked bovine tendon welds are extremely strong, capable of supporting greater than 10 to 20 $kg/cm^2$. This tensile strength rivals or exceeds that of suture repair of tendon without crosslinking.

In addition, crosslinked collagen is less susceptible to proteolytic attack, including collagenase, and is therefore remodelled slowly, which may provide a benefit to welded tissues because quick remodelling is believed to lead to a weakening of the weld area. Furthermore, the time at which crosslinking is initiated must be controlled when used in combination with thermal tissue welding such that crosslinking occurs only after thermal unwinding of the collagen fibrils begins.

Crosslinking may be achieved by chemical or photochemical methods and reagents. For example, glutaraldehyde is an excellent crosslinking agent, but is released from treated collagen as described in Speer et al., *J. Biomed. Materials Res.*, 14(6):753–764 (1980). Glutaraldehyde is also toxic in vivo. However, it has been used for chemosurgery in humans, and is widely and successfully used to crosslink animal collagens for human implantation as grafts, heart valves, and tissue fillers. After crosslinking, free glutaraldehyde is washed away, and lysine, or other compounds with free amine groups, is added to inactivate residual glutaraldehyde. A similar approach can be used in vivo with the present methods, e.g., using a 1 to 5% glutaraldehyde solution infiltrated into the weld site after thermal welding. Other chemical crosslinking agents include formaldehyde, dihydroxyacetone, and keto-sugars, e.g., D-ribose.

Another method of crosslinking, which allows control over both site and timing, is photochemical crosslinking. Methods of photochemical crosslinking include UV-C radiation (254 nm), UV-B radiation (280–320 nm), UV-A radiation (320–400 nm), and UV-A plus 8-methoxypsoralen, which is a well characterized bifunctional photochemical crosslinking agent. The benefit of such photochemical crosslinking is that an inactive crosslinking reagent can be applied to the weld site, and crosslinking does not commence until the reagent is activated by radiation. Such techniques are known in the art.

Heterobifunctional photochemical crosslinking agents have been used to photolabel structural proteins (Middaugh and Ji, *Eur. J. Biochem.* 110(2):587–592, 1980), and a recent report by Judy, *SPIE Proceedings* (1993, in press) suggests that UV-A initiated bifunctional crosslinking agents can be used to weld connective tissues. UV-A optical penetration into tissue is limited to only a few hundred $\mu m$ (Anderson et al., *J. Invest Dermatol.* 77:13–19 (1981)), and is thus useful primarily for small structures. Other heterobifunctional photo-activated crosslinking agents said to be biocompatible include 4-azidobenzoic acid N-hydroxysuccinimide ester (HSAB) and 6-(4-azido-2-nitrophenyl-amino) hexanoic acid N-hydroxysuccinimide ester (SANAH) available from Sigma Corp. These reagents are used as described in Nesburn et al., EPA 0,330,344.

An oxygen-dependent form of photochemical crosslinking, photodynamic crosslinking, may also work well in combination with thermal welding. For example, Spikes, *Photochem. Photobiol.*, 57(suppl):TPM-F36 (1993), recently reported an increase in rat tail tendon melting temperature from 63° C. to 67° C. after photodynamic photosensitization with visible light, using a variety of agents including sulfonated A1-phthalocyanine, chlorins, porphyrins, and xanthene dyes. Spikes concluded that extensive collagen crosslinking was involved. This method involves the use of photosensitizers that are activated by light, e.g., deeply-penetrating red light, are well tolerated in humans, do not interfere with connective tissue integrity or healing (Barr et al., *Photochem. Photobiol.* 46:795 (1987); Ortu et al., *Circulation* 85:1189–1196 (1992)), and are harmlessly metabolized.

One method of photodynamic crosslinking uses a 1 to 10% solution of methylene blue, a photodynamic dye used in humans for determining patency, leaks, etc., that is photo-activated by 670 nm red light. Methylene blue is an excellent generator of singlet oxygen but has little cell phototoxicity because it is rapidly inactivated by mitochondria. Methylene blue can also be iontophoresed into tissues easily in a few minutes, and is thus a good choice for use with the present methods.

Quenching After Welding

To further increase the tensile strength of a weld, the weld seam can be uniformly and rapidly cooled, or "quenched," immediately after heating. One method to quench the tissue junction region is by perfusing or spraying the weld site with ice-cold physiological saline immediately after the weld is complete. This quenching forces greater interactions across the weld seam to increase the weld strength by a factor of about two. Quenching may be followed by crosslinking as described above.

EXAMPLES

Fresh bovine achilles tendon, and fresh porcine skin, were cut into 2 mm thick transverse discs, which were placed between sealed microscope cover slides clamped gently together and immersed in a circulating water bath at different temperatures for different times. Other samples were welded in a moist atmosphere by heating between two stainless steel temperature-controlled plates instrumented with pressure and distance gages, with equivalent results. This model was used to determine weld strength after different crosslinking methods. A range of temperatures from 40° C. to 80° C. and times from 1 to 60 minutes were tested, with the strongest welds resulting from heating to about 60° C. for 30 minutes.

Figure 4:
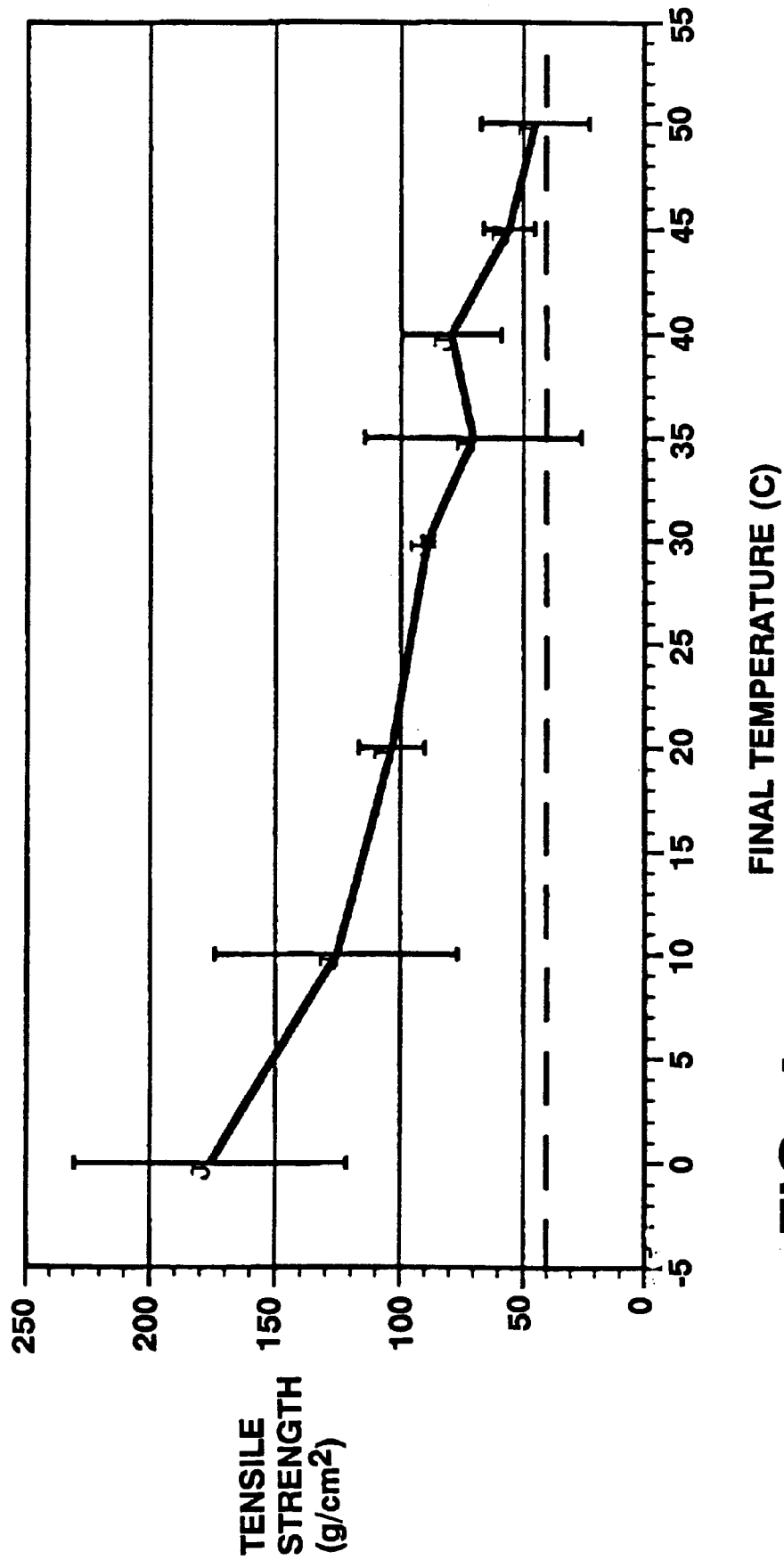
FIG. 4 is a graph showing the effects of quenching after welding.

After removal from the welding bath, some of the discs were quenched by immersion in a second bath at different temperatures, as low as 0° C., and then assayed for tensile strength by measuring the maximum force required to pull them apart under a slow loading rate. For example, FIG. 4 shows the effects of quenching on tensile strength of bovine tendon disc welds. Samples were heated for 4 minutes at 62° C. and cooled for ten minutes at the given temperatures. This was not the temperature required to obtain the strongest bond according to the invention. However, the strongest welds were obtained at 0° C. The dashed line at 40 $gm/cm^2$ in the graph shows the strongest "bonds" obtainable without heating, e.g., just bringing the wet discs into contact and allowing adhesive and cohesive forces to create a "bond." Interestingly, when the welded tissues were cooled over ten minutes from 62° C. to 50° C., the weld essentially separated.

Figure 5A:
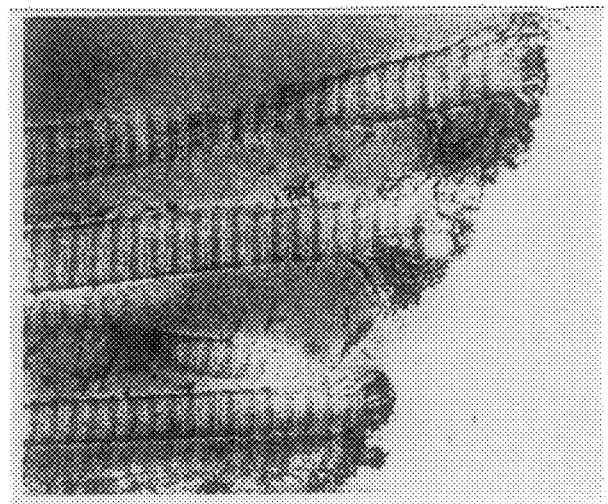
FIGS. 5A to 5C are transmission electron micrographs of a bovine tendon at various stages of separation and welding according to the methods of the invention.
Figure 5B:
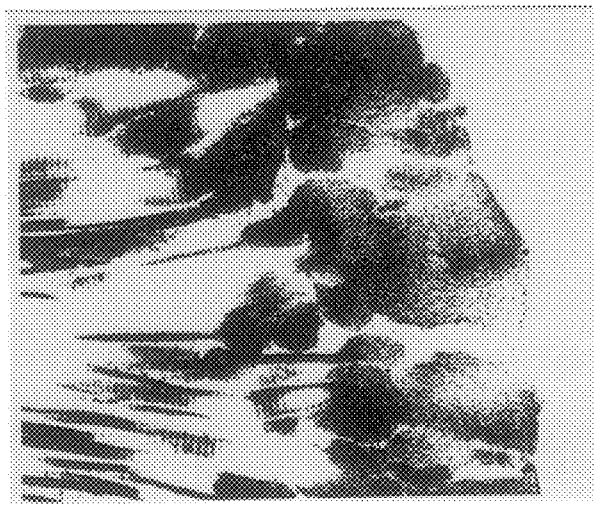
Figure 5C:
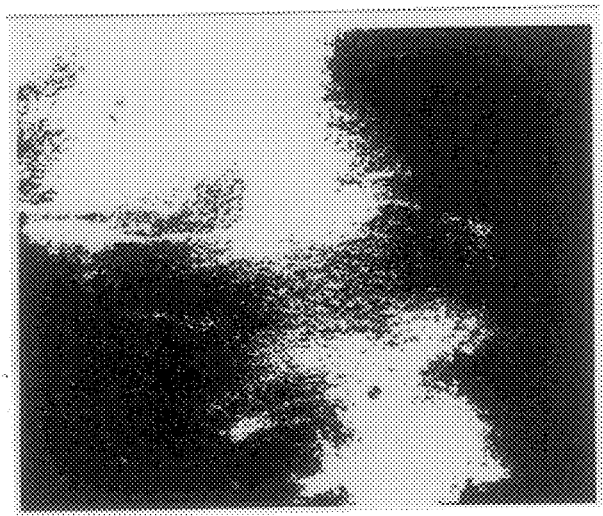

Electron microscopy was used to assess the structure of collagen fibrils in the region of the weld. Loss of birefringence from native collagen was measured using a polarized HeNe laser and linear polarized analyzer, and correlated with temperature and time. FIG. 5A shows a freshly cut, unheated tendon disc having the typical 70 nm banding pattern. The free ends are shown on the right side of the tissue. FIG. 5B shows a tendon after being uniformly heated to 60° C. for 3 minutes. As shown, only the outer 1 to 2 μm at the free ends of collagen fibrils were melted (right side of tissue), with loss of the 70 nm banding pattern. The remaining fibrils retained the banding pattern and were thus not denatured. As shown in FIG. 5C, an actual weld at 60° C. consists of an intermingling of the melted, unravelled, free ends of the fibrils across the gap between the two tendon discs. Only a region less than 2 μm is denatured, even though the entire tendon was uniformly heated.

At lower temperatures there was no change in fibrillar structure, and at higher temperatures, the entire tendon disc was affected and shrank (not shown) resulting in weak welds and/or tissue destruction.

Susceptibility of the weld to trypsin was also determined. In addition, the effect of chemical crosslinking of tissue proteins by 1% glutaraldehyde was studied both before and after attempting thermal welding. Eight bovine tendon discs were heated at 62° C. for ten minutes (not the temperature required for strongest weld). The resulting welds had a tensile strength of 200 (±50) gm/cm$^2$. Eight other samples heated in the same manner were subsequently treated with 1% glutaraldehyde for 12 hours and then rinsed. The resulting welds had a tensile strength of 950 (±300) gm/cm$^2$.

Preliminary studies also showed that simple thermal welds are susceptible to trypsin, which hydrolyses denatured collagen, but not native or helical collagen. With extensive chemical crosslinking, however, welds became more resistant to proteases, including collagenase. Welds resistant to proteases are likely to be remodeled much more slowly in vivo.

Thermal welding and healing, with or without crosslinking, also can be studied in vivo, e.g., in a rabbit tendon and skin model. Achilles tendon and skin incision welds are performed under several conditions of controlled temperature, clamp pressure, and quenching, and with and without crosslinking. Tissue welds from this study are prepared for histology and electron microscopy, and analyzed for tensile strength for comparison with in vitro welds.

A healing study, e.g., is conducted in the same model with sutured incisions as a control. Tissue remodelling is assessed by histology and electron microscopy, and tensile strength is assessed by destructive tensiometry and biochemical assays. Tissue not used for pathology is saved and used for analysis by SDS-PAGE of protein hydrolysate, and procollagen mRNA.

To study vessel welding, fresh porcine mesenteric vessels 1 to 5 mm in diameter (measured at 100 mm Hg pressure) are tested in a simple apparatus which applies both controlled pressure and controlled temperature to a segment of vessel clamped between two flat stainless steel plates. Two circulating water baths are used to dynamically control the device temperature.

A micro-thermocouple is used to determine the thermal time constant for heating the tissue between the "jaws" of the clamping device as a function of the distance between the jaws. The thermal time constant in seconds is about equal to the square of the tissue thickness in millimeters. Most blood vessels have 1 mm or thinner walls; therefore, a uniform temperature within 2° C. of the target temperature should take at most ten seconds to achieve. Parameters of clamp pressure, temperature, and tissue deformation are monitored dynamically through transducers in the apparatus. Temperature, time, pressure, and cooling rate are systematically varied to produce welds, which are then tested by measuring the intraluminal bursting pressure. Histology and transmission electron microscopy are also used to monitor results.

USE

The methods of the invention can be used to join two different collagen-containing materials or two pieces of the same material. The methods can be used in vivo to repair cut tissues as well as implanting a collagen-containing (or covered) prosthesis to surrounding tissue in an animal or human. In addition, the methods can be used in vitro to manufacture prostheses or other devices made of collagen. The two materials can be apposed by standard techniques, e.g., with clamps, forceps, molds, or mandrils, during the heating procedure.

In addition to providing a mechanism by which tissues can be repaired without the need for any sutures or other closure methods, the present methods can also be used as an adjunct to traditional tissue closure methods, since welding results in an actual sealing of the gap between the cut surfaces of two materials.

OTHER EMBODIMENTS

Other embodiments are within the following claims.

I claim:

1. A method of permanently joining a first, solid, biological, collagen-containing material to a second, solid collagen-containing material, each material having free ends of collagen fibrils at a surface, said method comprising the steps of bringing the free ends of collagen fibrils at the surfaces of the first and second materials into contact, heating the first and second materials for a time and to a temperature sufficient to permanently join the first and second materials at an area of contact of the free ends, wherein said temperature is above a melting temperature of the collagen fibril free ends, and below a melting temperature of intact collagen fibrils, such that collagen fibrils in the first and second materials are not denatured except at their free ends, and thereafter crosslinking the collagen along said area of contact, said crosslinking being achieved by applying a photodynamic photosensitizer and then applying radiation to said area of contact.

2. The method of claim 1, wherein said photodynamic photosensitizer is a phthalocyanine, chlorin, porphyrin, 8-methoxypsoralen, xanthene dye, or thiazine dye.

3. The method of claim 2, wherein said photodynamic photosensitizer is methylene blue.

4. A method of permanently joining a first, solid, biological, collagen-containing material to a second, solid collagen-containing material, each material having free ends of collagen fibrils at a surface, said method comprising the steps of bringing the free ends of collagen fibrils at the surfaces of the first and second materials into contact, heating the first and second materials for a time and to a temperature sufficient to permanently join the first and second materials at an area of contact of the free ends, wherein said temperature is above a melting temperature of the collagen fibril free ends, and below a melting temperature of intact collagen fibrils, such that collagen fibrils in the first and second materials are not denatured except at their free ends, and thereafter crosslinking the collagen along said area of contact, said heating being achieved by electrical resistance, circulating fluid, radio frequency current, microwaves, ultrasound, or infrared or optical radiation.

5. The method of claim 1, wherein said first and second materials are the same.

6. The method of claim 1, wherein said first material is a biological tissue and said second material is a non-living, collagen-containing prosthesis.

7. A method of permanently joining a first, solid, biological, collagen-containing material to a second, solid collagen-containing material, each material having free ends of collagen fibrils at a surface, said method comprising the steps of bringing the free ends of collagen fibrils at the surfaces of the first and second materials into contact, heating the first and second materials for a time and to a temperature sufficient to permanently join the first and second materials at an area of contact of the free ends, wherein said temperature is above a melting temperature of the collagen fibril free ends, and below a melting temperature of intact collagen fibrils, such that collagen fibrils in the first and second materials are not denatured except at their free ends, and thereafter crosslinking the collagen along said area of contact, said crosslinking being achieved by applying ultraviolet radiation to said area of contact.

* * * * *